(12) United States Patent
Gibson et al.

(10) Patent No.: US 6,548,672 B1
(45) Date of Patent: Apr. 15, 2003

(54) PREPARATION OF POLYMERISATION CATALYSTS

(75) Inventors: Vernon Charles Gibson, London (GB); Stuart James McTavish, London (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/669,726

(22) Filed: Sep. 26, 2000

Related U.S. Application Data

(63) Continuation of application No. PCT/GB99/02498, filed on Jul. 30, 1999.

(30) Foreign Application Priority Data

Aug. 6, 1998 (GB) .............................................. 9817004

(51) Int. Cl.⁷ .......................... C07F 15/02; C07F 15/06; C07F 13/00; C07F 15/00
(52) U.S. Cl. .......................................... 546/12; 546/10
(58) Field of Search ..................... 546/10, 12

(56) References Cited

U.S. PATENT DOCUMENTS

| | | | | |
|---|---|---|---|---|
| 5,506,326 A | * | 4/1996 | Kneafsey | 525/126 |
| 5,955,555 A | * | 9/1999 | Bennett | 526/133 |
| 6,063,881 A | * | 5/2000 | Bennett | 526/161 |
| 6,350,916 B1 | * | 2/2002 | Guram et al. | 568/320 |
| 6,414,098 B1 | * | 7/2002 | Engehausen et al. | 502/104 |
| 6,461,994 B1 | * | 10/2002 | Gibson et al. | 502/155 |
| 6,462,152 B1 | * | 10/2002 | Berardi et al. | 526/75 |

FOREIGN PATENT DOCUMENTS

| WO | WO 98/27124 | 6/1998 |
|---|---|---|

OTHER PUBLICATIONS

Brooker, J. Chem Soc. Dalton Trans 2397 (1990).*
Bonardi, Inorg Chimica Acta 232, 211 (1995).*
Curry, Inorg. Chem 6, 1570 (1967).*
Black et al., Template Synthesis of Metal Complexes Containing New Macrocyclic Ligand Systems, Tetrahedron Letters, No. 31, pp. 2835–2836, (1978).
Condensed Chemical Dictionary, 10th edition, pp. 193, 525, 977.*

* cited by examiner

*Primary Examiner*—Mark L. Berch
(74) *Attorney, Agent, or Firm*—Finnegan, Henderson, Farabow, Garrett and Dunner, L.L.P.

(57) ABSTRACT

A process for producing a transition metal complex of formula (B) wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^6$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, the two or more can be linked to form one or more cyclic substituents; comprising reacting together in a single stage reaction components comprising (1) precursors capable of forming Ligand (B) and (2) a compound of the formula M[T]-(T/b)X. The complex can be used as a catalyst for the polymerisation of 1-olefins.

16 Claims, No Drawings

PREPARATION OF POLYMERISATION CATALYSTS

RELATED APPLICATIONS

This application is a continuation of international application No. PCT/GB99/02498 filed Jul. 30, 1999.

BACKGROUND OF THE INVENTION

The present invention relates to a novel process for preparing transition metal compounds used as polymerisation catalysts.

The use of certain transition metal compounds to polymerise 1-olefins, for example, ethylene, is well established in the prior art. The use of Ziegler-Natta catalysts, for example, those catalysts produced by activating titanium halides with organometallic compounds such as triethylaluminium, is fundamental to many commercial processes for manufacturing polyolefins. In recent years the use of certain metallocene catalysts (for example biscyclopentadienylzirconiumdichloride activated with alumoxane) has provided catalysts with potentially high activity and capable of providing an improved distribution of the comonomer units. Most recently, WO98/27124 has disclosed that ethylene may be polymerised by contacting it with certain iron or cobalt complexes of selected 2,6-(pyridinecarboxaldehydebis(imines) and 2,6-diacylpyridinebis(imines); and our own copending application WO 99/12981 has disclosed novel nitrogen-containing transition metal compounds comprising the skeletal unit depicted in Formula B:

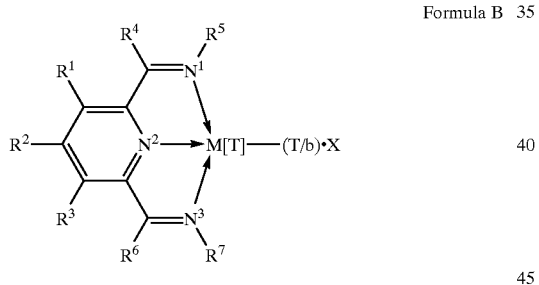

Formula B wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1, R^2, R^3, R^4, R^5, R^6$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents.

The above transition-metal complexes are disclosed as being made by first forming the ligand (eg Examples 1 to 6 of WO 98/27124) and then separately reacting the ligand with the desired metal salt such as $FeCl_2$ or $CoCl_2$ (eg Examples 7 to 17 of WO 98/27124) to form the complex. This route is also exemplified in WO 99/12981, for example in the synthesis of 2,6-diacetylpyridinebis(2,6-diisopropylanil)FeCl₂ (Formula D below), where the reaction scheme is shown as follows:

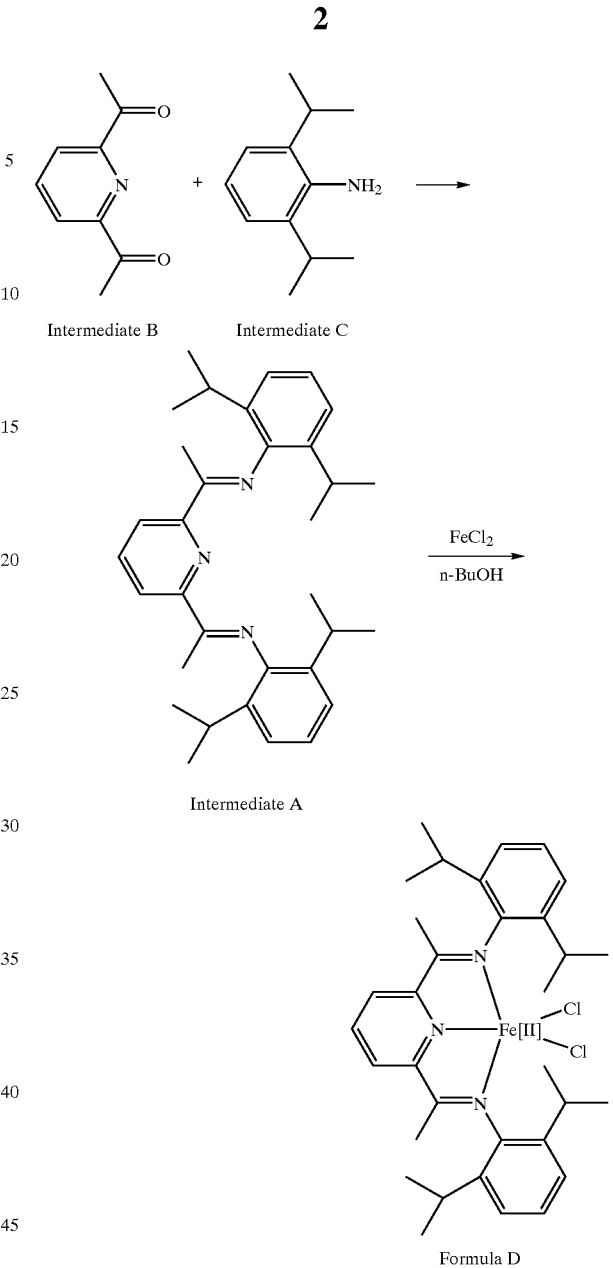

Hitherto, it has been considered necessary to complete the reaction between Intermediates B and C to form Intermediate A (the ligand), and to isolate Intermediate A from Intermediates B and C prior to reacting with the transition metal compound to form the transition metal complex compound (Formula B). However we have now discovered that this two step process can in fact be performed as a single stage reaction, using, for example, a single reaction vessel. This provides substantial process and economic advantages.

SUMMARY OF THE INVENTION

Accordingly a first aspect of the present invention provides a process for producing a transition metal complex of the formula

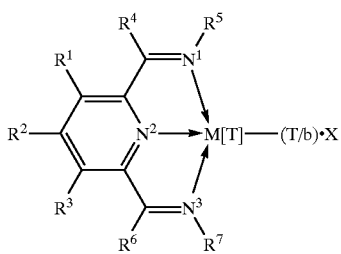

Formula B

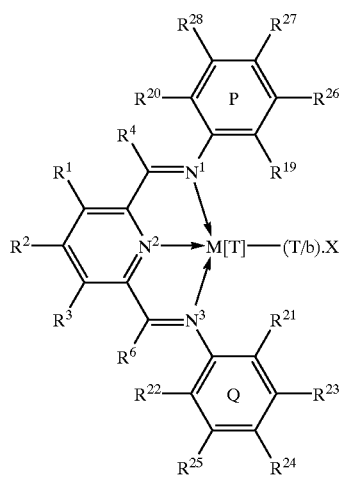

Formula Z wherein M is Fe[II], Fe[III], Co[I], Co[II], Co[III], Mn[I], Mn[II], Mn[III], Mn[IV], Ru[II], Ru[II] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^6$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents;

comprising reacting together in a single stage reaction components comprising (1) precursors capable of forming Ligand B

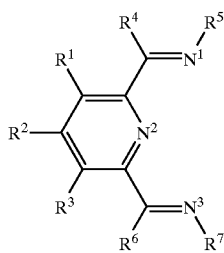

Ligand B and (2) a compound of the formula M[T]-(T/b)X.

The reaction is preferably carried out in a single reaction vessel.

In the process of the present invention, the final product is obtained directly in a single stage reaction, without the need for any additional process steps: however at a molecular level the reaction may of course still proceed through more than one step.

DETAILED DESCRIPTION OF THE INVENTION

Preferred transition metal complexes to be made by the process of the present invention comprise the skeletal unit depicted in Formula Z:

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^4$, $R^6$ and $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system. In this particular aspect of the present invention, in the case that neither of the ring systems P and Q forms part of a polyaromatic ring system, it is preferred that at least one of $R^{19}$ and $R^{20}$, and at least one of $R^{21}$ and $R^{22}$ is selected from hydrocarbyl, substituted hydrocarbyl, heterohydrocarbyl or substituted heterohydrocarbyl, and most preferably each of $R^{19}$, $R^{20}$, $R^{21}$ and $R^{22}$ is selected from hydrocarbyl, substituted hydrocarbyl, heterohydrocarbyl or substituted heterohydrocarbyl. The atom or group represented by X is preferably halide, sulphate, nitrate, thiolate, thiocarboxylate, $BF_4^-$, $PF_6^-$, hydride, hydrocarbyloxide, carboxylate, hydrocarbyl, substituted hydrocarbyl and heterohydrocarbyl. Examples of such atoms or groups are chloride, bromide, methyl, ethyl, propyl, butyl, octyl, decyl, phenyl, benzyl, methoxide, ethoxide, isopropoxide, tosylate, triflate, formate, acetate, phenoxide and benzoate.

Subject to the foregoing provisos regarding $R^{19}$, $R^{20}$, $R^{21}$ and $R^{22}$ in Formula Z, $R^1$ to $R^4$, $R^6$ and $R^{19}$ to $R^{28}$ in the compounds depicted in Formulae B and Z of the present invention are preferably independently selected from hydrogen and $C_1$ to $C_8$ hydrocarbyl, for example, methyl, ethyl, n-propyl, n-butyl, n-hexyl, and n-octyl. In Formula B, $R^5$ and $R^7$ are preferably independently selected from substituted or unsubstituted alicyclic, heterocyclic or aromatic groups, for example, phenyl, 1-naphthyl, 2-naphthyl, 2-methylphenyl, 2-ethylphenyl, 2,6-diisopropylphenyl, 2,3-diisopropylphenyl, 2,4-diisopropylphenyl, 2,6-di-n-butylphenyl, 2,6-dimethylphenyl, 2,3-dimethylphenyl, 2,4-dimethylphenyl, 2-t-butylphenyl, 2,6-diphenylphenyl, 2,4,6-trimethylphenyl, 2,6-trifluoromethylphenyl, 4-bromo-2,6-dimethylphenyl, 3,5 dichloro2,6-diethylphenyl, and 2,6,bis (2,6-dimethylphenyl)phenyl, cyclohexyl and pyridinyl.

The ring systems P and Q in Formula Z are preferably independently 2,6-hydrocarbylphenyl or fused-ring polyaromatic, for example, 1-naphthyl, 2-naphthyl, 1-phenanthrenyl and 8-quinolinyl.

A further aspect of the present invention provides process for producing a transition metal complex having the Formula T:

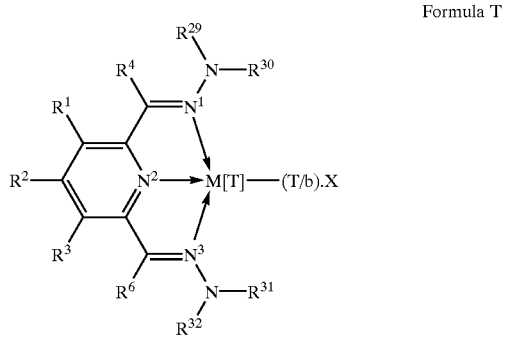

Formula T wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$ to $R^4$, $R^6$ and $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents, comprising reacting together in a single stage reaction components comprising (1) precursors capable of forming Ligand T

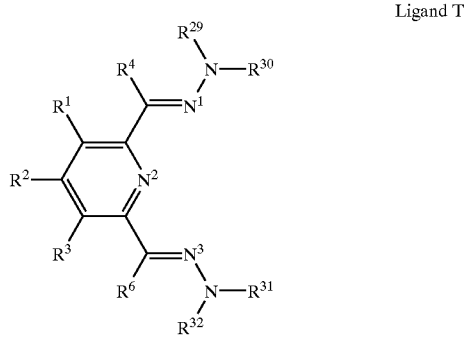

Ligand T and (2) a compound of the formula M[T]-(T/b)X.

Examples of complexes which may be made by the process of the invention include 2,6-diacetylpyridinebis(2,6-diisopropylanil)FeCl$_2$, 2,6-diacetylpyridinebis(2,4,6-trimethylanil)FeCl$_2$, 2,6-diacetylpyridine(2,6-diisopropylanil)CoCl$_2$, 2,6diacetylpyridinebis(2,4,6-trimethylanil)CoCl$_2$, 2,6-diacetylpyridinebis(2,6-dimethylanil)FeCl$_2$, and 2,6-diacetylpyridinebis(2,4-dimethylanil) FeCl$_2$.

In the process of the present invention it is preferred that the components (1) and (2) of the reaction are brought together substantially simultaneously. However, if desired, they may be brought together in quick succession in any order.

Preferably the reaction between components (1) and (2) is carried out in the presence of an acidic catalyst. Examples of acidic catalysts include glacial acetic acid, p-toluenesulphonic acid and formic acid.

It is preferred to carry out the reaction in the presence of a liquid diluent. Most preferably the diluent is a solvent for one or more of the components of the reaction. Examples of suitable liquid diluents are liquid hydrocarbons, for example toluene, xylene, hexane and cyclohexane, or alcohols, for example, ethanol, isopropanol or 1-butanol.

The reaction is preferably carried out at temperatures between 0° C. and 150° C. Preferably the reaction is heated, typically to a temperature between 50° C. and 130° C., more usually to between 70 to 110° C.

The time for the reaction may be, for example, from 5 minutes to 72-hours, though it is more usually between 12 and 48 hours, typically 18 to 36 hours.

The ligand precursors employed in the reaction process of the present invention to make the "Ligand B" preferably comprise a compound of the Formula K

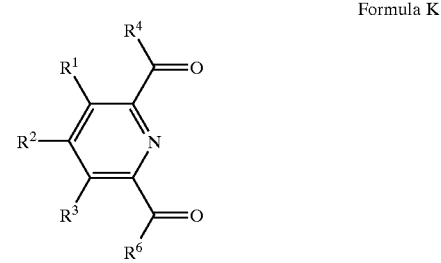

Formula K plus compounds H$_2$NR$^5$ and H$_2$NR$^7$, where $R^1$ to $R^7$ are as defined above. When $R^1$ and $R^7$ are the same, two equivalents of the same amine compound are of course used. When $R^5$ and $R^7$ are the different and two amines are used, a mixture of products may be obtained, with $R^5$ and $R^7$ being either the same or different on an individual molecule. The ligand precursors employed in the reaction to make the "Ligand T" preferably comprise a compound of the Formula K

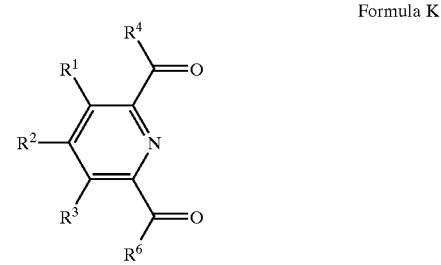

Formula K plus compounds H$_2$N—NR$^{29}$R$^{30}$ and H$_2$N—NR$^{31}$R$^{32}$, where $R^1$ to $R^4$, $R^6$, $R^{29}$, $R^{30}$, $R^{31}$ and $R^{32}$ are as defined above. When H$_2$N—NR$^{29}$R$^{30}$ and H$_2$N—NR$^{31}$R$^{32}$ are the same, two equivalents of the same amine compound are used. When H$_2$N—NR$^{29}$R$^{30}$ and H$_2$N—NR$^{31}$R$^{32}$ are the different, a mixture of products may be obtained, with —NR$^{29}$R and —NR$^{31}$R$^{32}$ being either the same or different on an individual molecule.

In the process of the present invention, M and X in the compound of the formula M[T]-(T/b)X [component (2)] are as defined in the Formulae B, Z and T as set out above. Examples of compounds of the formula M[T]-(T/b)X are FeCl$_2$, MnCl$_2$, CoCl$_2$, FeBr$_2$, CoBr$_2$ and FeCl$_3$. Preferred metals M[T] are Fe[II], Fe[III], Co[II] and Co[III].

The process of the present invention can be used to produce mixtures of complexes containing two or more different transition metals, for example, by employing two or more different transition metal compounds of formula M[T]-(T/b)X as the component (2).

The complexes made according to the process of the invention may be used directly as polymerisation catalysts. Alternatively they may be combined with an activator. The activator compound is suitably selected from organoaluminium compounds and hydrocarbylboron compounds. Suitable organoaluminium compounds include trialkylaluminium compounds, for example, trimethylaluminium, triethylaluminium, tributylaluminium, tri-n-octylaluminium, ethylaluminium dichloride, diethylaluminium chloride and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof Commercially available alumoxanes are generally believed to be mixtures of linear and cyclic compounds. The cyclic alumoxanes can be represented by the formula $[R^{16}AlO]_s$ and the linear alumoxanes by the formula $R^{17}(R^{18}AlO)_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups.

Examples of suitable hydrocarbylboron compounds are dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)[(bis-3,5-trifluoromethyl)phenyl]borate$, trityltetra(pentafluorophenyl)borate and tris(pentafluorophenyl) boron.

The quantity of activating compound selected from organoaluminium compounds and hydrocarbylboron compounds for the process for making the polymerisation catalyst is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per Fe, Co, Mn or Ru metal atom in the compound of Formula B.

If desired, the preparation of the polymerisation catalyst can be carried out in the same vessel as the preparation of the transition metal complex by the process of the present invention.

Catalysts made with complexes prepared according to the present invention can be unsupported or supported on a support material, for example, silica, alumina, or zirconia, or on a polymer or prepolymer, for example polyethylene, polystyrene, or poly(aminostyrene). If desired the catalysts can be formed in situ in the presence of the support material, or the support material can be pre-impregnated or premixed, simultaneously or sequentially, with one or, more of the catalyst components. The catalysts can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The quantity of support material employed can vary widely, for example from 100,000 to 1 grams per gram of metal present in the transition metal compound.

If it is desired to use the catalyst on a support material (see below), this can be achieved, for example, by preforming the catalyst system comprising the transition metal complex and the activator and impregnating the support material preferably with a solution thereof, or by introducing to the support material one or more of the components simultaneously or sequentially.

EXAMPLES

Preparation of Complexes 2,6-pyridyldiimine iron(II)dichloride complexes of the formula below were produced by the process of the invention.

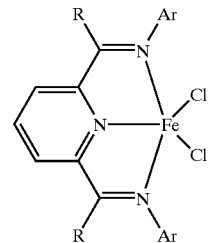

1 R = H, Ar = 2,4,6-trimethylanil
2 R = Me, Ar = 2,4,6-trimethylanil
3 R= H, Ar = 2,6-diethylanil

Example 1

Preparation of 1-[2,6-Dialdiminepyridinebis(2,4,6-trimethylanil) $FeCl_2$]

To a schlenk tube, under a nitrogen atmosphere, 2,6-pyridinedicarboxaldehyde (1.2 equivs, 0.054 g, 0.397 mmol), anhydrous iron(II)dichloride (1 eq, 0.042 g, 0.331 mmol) and 2,4,6-trimethylaniline (25 eq, 0.12 ml, 0.828 mmol) were added followed by n-butanol (40 ml, dry) to form a yellow suspension. The reaction mixture was heated at 80° C. for 20 h to produce a brown precipitate. Solvent removed at the pump and the residue washed, ether (6×30 ml) to yield a brown solid (0.101 g, 62%), 1. $FAB^+$ MS m/z 495 [$M^+$-], 460 [$M^+$-Cl], 422 [$M^+$-2Cl], 368 [$M^+$-$FeCl_2$].

IR ν(C=N) 1632 $cm^{-1}$. No other C=N peaks were observed in the IR.

Example 2

Preparation of 2-[2,6-Diacetylpyridinebis(2,4,6-trimethylanil) $FeCl_2$]

To a schlenk tube, under a nitrogen atmosphere, 2,6-diacetylpyridine (1.2 eq, 0.054 g, 0.397 mmol), anhydrous iron(II)dichloride (1 eq, 0.042 g, 0.331 mmol), 2,4,6-trimethylaniline (2.5 eq, 0.12 ml, 0.828 mmol) and glacial acetic acid (3 drops, catalyst) were added followed by n-butanol (40 ml, dry). The reaction mixture was heated at 80° C. for 24 h to produce a dark blue precipitate. Solvent removed at the pump and the residue washed, ether (4×30 ml) to yield a dark blue solid (0.137 g, 83%), 2. FAB+ MS m/z 523 [M+-], 488 [M+-Cl], 453 [M+-2Cl]

Example 3

Preparation of 3-[2,6-Diacetylpyridinebis(2,6-diethylanil) FeCl$_2$]

Anhydrous iron(II)dichloride (0.095 g, 0.750 mmol) 2,6-pyridinedicarboxaldehyde (1.2 eq, 0.122 g, 0.900 mmol), and 2,6-diethylaniline (2.5 eq, 0.310 ml, 1.875 mmol) were added to a Schlenk tube, followed by n-butanol (40ml), and were heated at 80° C. for 48 h. A green precipitate appeared after 10 min. Solvent was removed at the pump to yield, upon washing with ether (4×40 m1), a green solid. FAB+ MS m/z 523 [M+], 488 [M+-Cl], 453 [M+-2Cl].

Polymerisation Using Complexes Prepared Above

To a Schlenk tube, catalyst (0.01 mmol) and toluene (40 ml, dry) were added followed by methylalumoxane (10%w/w in toluene, 100 eq, 0.65 ml, 1.00 mmol) to form an orange solution. The Schlenk tube was placed in a water bath at ambient temperature. Ethylene atmosphere (1 bar) was passed over the solution for 30 minutes. The reaction was then quenched by addition of dilute HCl (40 ml), and the resulting polymer filtered and washed with methanol (3×50 ml) to yield, upon drying in vacuum oven, solid polyethylene.

Example 4

Polymerisation using 1-[2,6-Dialdiminepyridinebis(2,4,6-trimethylanil) FeCl$_2$]

Complex 1, (0.01 mmol, 4.96 mg), yielded 6.20 g polyethylene giving an activity of 1240 gmmol$^{-1}$h$^{-1}$bar$^{-1}$.

PE, M$_W$=46000, PDI=18.0, M$_{PK}$=1400

Example 5

Polymerisation using 2-[2,6-Diacetylpyridinebis(2,4,6-trimethylanil) FeCl$_2$]

Complex 2, (0.01 mmol, 5.24 mg), yielded 4.35 g polyethylene giving an activity of 870 gmmol$^1$h$^1$bar$^1$.

PE, M$_W$=80 000, PDI=21.0, M$_{PK}$=70 000.

These results show that the process of the invention provides catalysts which are as effective as those produced by the known two-stage process.

We claim:

1. Process for producing a transition metal complex of the formula

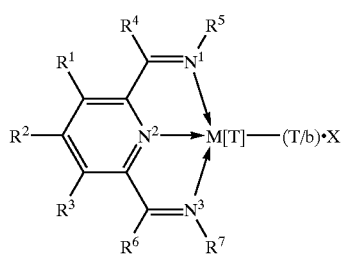

Formula B wherein M is Fe[II], Fe[III], Co[I], Co[II], Co[III], Mn[I], Mn[II], Mn[III], Mn[IV], Ru[II], Ru[III] or Ru[IV]; X is halide, sulphate, nitrate, thiolate, thiocarboxylate, BF$^-_4$, PF$^-_6$, triflate, tosylate, hydride, hydrocarbyloxide or carboxylate covalently or ionically bonded to the transition metal M; T is the oxidation state of the transition metal M and b is the valency of the atom or group X; $R^1$, $R^2$, $R^3$, $R^4$, and $R^6$ are independently selected from hydrogen, halogen, or hydrocarbyl; and when any two or more of $R^1$–$R^4$ and $R^6$ are hydrocarbyl, said two or more can be linked to form one or more cyclic substituents; and $R^5$ and $R^7$ are selected from either the rings P and Q respectively,

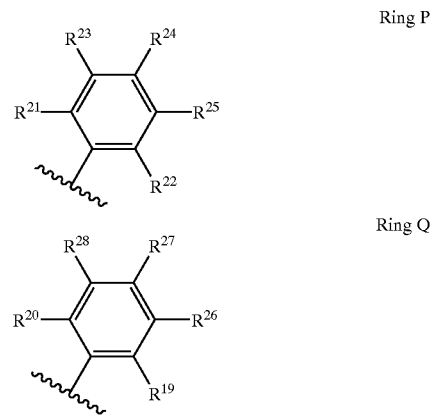

Ring P

Ring Q wherein $R^{19}$ to $R^{28}$ are independently selected from hydrogen, halogen or hydrocarbyl, and when any two or more thereof are hydrocarbyl, said two or more can be linked to form one or more cyclic substituents; with the proviso that at least one of $R^{19}$, $R^{20}$, $R^{21}$ and $R^{22}$ is hydrocarbyl when neither of the ring systems P and Q forms part of a polyaromatic fused-ring system; or —NR$^{29}$R$^{30}$ and —NR$^{31}$R$^{32}$ respectively, wherein $R^{29}$ to $R^{32}$ are independently selected from hydrogen, or hydrocarbyl; and when any two or more thereof are hydrocarbyl, said two or more can be linked to form one or more cyclic substituents;

comprising reacting together in a single stage reaction components comprising (1) precursors capable of combining to form Ligand B directly

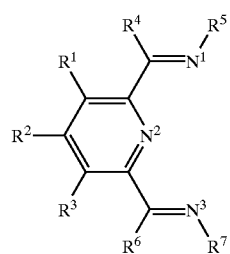

Ligand B and (2) a compound of the formula MM-(T/b)X.

2. Process according to claim 1 which is carried out in a single reaction vessel.

3. Process according to claim 1 wherein $R^1$ to $R^4$ and $R^6$ and $R^{19}$ to $R^{28}$ are independently selected from hydrogen, methyl, ethyl, n-propyl, n-butyl, n-hexyl and n-octyl.

4. Process according to claim 1 wherein the reaction between components (1) and (2) is carried out in the presence of an acidic catalyst.

5. Process according to claim 4 wherein the acidic catalyst comprises glacial acetic acid, p-toluenesulphonic acid or formic acid.

6. Process according to claim 1 wherein the reaction is carried out in the presence of a liquid diluent.

7. Process according to claim 6 wherein the diluent comprises toluene, xylene, hexane, cyclohexane, ethanol, isopropanol or 1-butanol.

8. Process according to claim 1 wherein the reaction is carried out at a temperature of from 50° C. to 130° C.

9. Process according to claim 1 wherein the transition metal complex has the skeletal unit depicted in Formula Z:

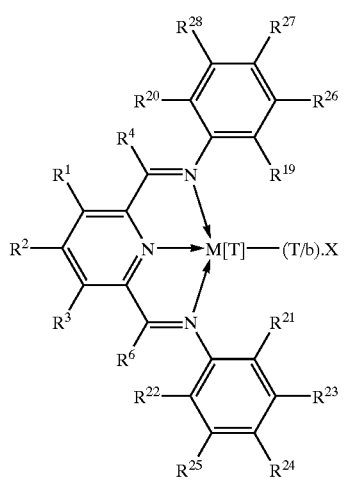

Formula Z

10. Process according to claim 9 wherein the reactants comprise
(1a) a compound of the Formula K

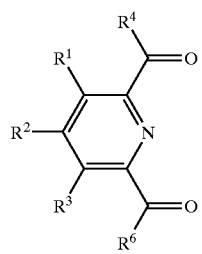

Formula K (1b) compounds having the formulae $H_2NR^5$ and $H_2NR^7$ where $R^5$ and $R^7$ are selected from either the rings P and Q respectively; and (2) a compound of the formula M[T]-(T/b)X.

11. Process according to claim 1 wherein $R^5$ and $R^7$ are independently selected from phenyl, 1-naphthyl, 2-naphthyl, 2-methylphenyl, 2-ethylphenyl, 2,6-diisopropylphenyl, 2,3-diisopropylphenyl, 2,4-diisopropylphenyl, 2,6-di-n-butylphenyl, 2,6-dimethylphenyl, 2,3-dimethylphenyl, 2,4-dimethylphenyl, 2-t-butylphenyl, 2,6-diphenylphenyl, 2,4,6-trimethylphenyl, 2,6-trifluoromethylphenyl, 4-bromo-2,6-dimethylphenyl, 3,5 dichloro2,6-diethylphenyl, and 2,6, bis(2,6-dimethylphenyl)phenyl.

12. Process according to any of claim 1 wherein the transition metal complex has the skeletal unit depicted in Formula T:

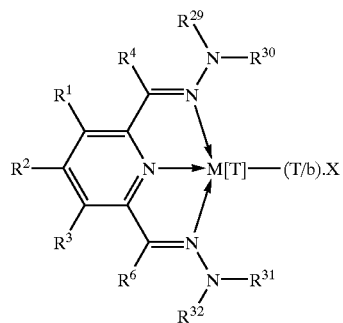

Formula T

13. Process according to claim 12 wherein the reactants comprise (1a) a compound of the Formula K

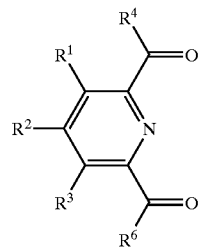

Formula K (1b) compounds having the formulae $H_2N\text{---}NR^{29}R^{30}$ and $H_2N\text{---}NR^{31}R^{32}$; and (2) a compound of the formula M[T]-(T/b)X.

14. Process according to claim 1 wherein the transition metal complex comprises 2,6-diacetylpyridinebis(2,6-diisopropylanil)FeCl$_2$, 2,6-diacetylpyridinebis(2,4,6-trimethylanil)FeCl$_2$, 2,6-diacetylpyridine(2,6-diisopropylanil)CoCl$_2$, 2,6-diacetylpyridinebis(2,4,6-trimethylanil)FeCl$_2$, 2,6-diacetylpyridinebis(2,6-dimethylanil)FeCl$_2$, or 2,6-diacetylpyridinebis(2,4-dimethylanil)FeCl$_2$.

15. Process according to claim 1 wherein X comprises chloride, bromide, methoxide, ethoxide, isopropoxide, tosylate, triflate, formate, acetate, phenoxide and benzoate.

16. Process according to claim 1 wherein M[T] comprises Fe[II], Fe[III], Co[II] or Co[III].

* * * * *

UNITED STATES PATENT AND TRADEMARK OFFICE
CERTIFICATE OF CORRECTION

PATENT NO. : 6,548,672 B1
DATED : April 15, 2003
INVENTOR(S) : Vernon Charles Gibson It is certified that error appears in the above-identified patent and that said Letters Patent is hereby corrected as shown below:

<u>Column 9,</u>
Line 67, "tonically" should read -- ionically --.

<u>Column 10,</u>
Line 56, "MM-(T/b)X." should read -- M[T]-(T/b)X. --.

Signed and Sealed this

Eighteenth Day of November, 2003

JAMES E. ROGAN
*Director of the United States Patent and Trademark Office*